United States Patent
Albert et al.

(10) Patent No.: US 11,883,455 B2
(45) Date of Patent: Jan. 30, 2024

(54) ***NIGELLA SATIVA* OIL COMPOSITION**

(71) Applicant: N.S. OILS LTD., Kibbutz Sa'ad (IL)

(72) Inventors: Rotem Albert, Kibbutz Mefalsim (IL); Gidon Albert, Kibbutz Sa'ad (IL); Dani Rapaport, Kfar Haroe'e (IL); Mor Zeilkha, Ramat Gan (IL)

(73) Assignee: N.S. OILS LTD., Kibbutz Sa'ad (IL)

( * ) Notice: Subject to any disclaimer, the term of this patent is extended or adjusted under 35 U.S.C. 154(b) by 0 days.

(21) Appl. No.: 16/981,049

(22) PCT Filed: Mar. 20, 2019

(86) PCT No.: PCT/IL2019/050316
§ 371 (c)(1),
(2) Date: Sep. 15, 2020

(87) PCT Pub. No.: WO2019/180719
PCT Pub. Date: Sep. 26, 2019

(65) Prior Publication Data
US 2021/0015880 A1    Jan. 21, 2021

Related U.S. Application Data

(60) Provisional application No. 62/645,201, filed on Mar. 20, 2018.

(51) Int. Cl.
*A61K 36/71* (2006.01)
*A61K 9/00* (2006.01)

(52) U.S. Cl.
CPC .......... *A61K 36/71* (2013.01); *A61K 9/0053* (2013.01)

(58) Field of Classification Search
None
See application file for complete search history.

(56) References Cited

U.S. PATENT DOCUMENTS

2015/0004266 A1 * 1/2015 Babish .................. A61K 36/71
424/776

FOREIGN PATENT DOCUMENTS

EP    2049132 B1    12/2012
WO    2013/030669 A2    3/2013

OTHER PUBLICATIONS

Benkaci-Ali et al. (2007) Flavour Fragr. J. 22: 148-153. (Year: 2007).*
Sudhir et al. (2017) International J. Pharmacy and Biol. Sci. vol. 7, Issue 2,: 131-144. (Year: 2017).*
Toma et al. (2010) Farmacia vol. 58, 4: 458-464. (Year: 2010).*
Ahmad et al. (2013) Asian Pac. J. Trop. Biomed. 3(5): 337-352. (Year: 2013).*
D'Antuono et al. (2002) Industrial Crops and Products 15: 59-69. (Year: 2002).*
Hassanien et al. (2014) Eur. J. Lipid Sci. Technol. 116: 1563-1571. (Year: 2014).*
Kokoska et al. (2008) J. Food Protection vol. 71, No. 12: 2475-2480. (Year: 2008).*
Mohammed Nameer Khairulla et al.; "The effects of different extraction methods on antioxidant properties, chemical composition and thermal behavior of black seed (*Nigella sativa* L.) oil"; Evidence-based Complementary and Alternative Medicine; Hindawi Publishing Corp.; vol. 2016: 1, Jan. 2016; pp. 6273817-1.
Rahmani, A.H. et al.; "Nigella sativa and its active constituent thymoquinone show pivotal role in the diseases prevention and treatment"; Asian Journal of Pharmaceutical and Clinical Research; vol. 8 (1) Jan. 1, 2015; pp. 48-53.

* cited by examiner

*Primary Examiner* — Russell G Fiebig
(74) *Attorney, Agent, or Firm* — BROWDY AND NEIMARK, PLLC

(57) ABSTRACT

The present invention is directed to composition comprising *Nigella sativa* (NS) oil, wherein said oil comprises thymoquinone (TQ) at a concentration of at least 2% (w/w). The composition is further characterized by having a much lower free fatty acid concentration than prior art compositions. The composition, which has anti-inflammatory activity, may be formulated for oral administration to a mammalian subject, for the purpose of preventing or treating inflammatory conditions and other disorders.

7 Claims, 4 Drawing Sheets

NIGELLA SATIVA OIL COMPOSITION

FIELD OF THE INVENTION

The present invention is directed to compositions containing oil obtained from *Nigella sativa*.

BACKGROUND OF THE INVENTION

*Nigella sativa* (NS), also known by a variety of other names, including black cumin, black seed and black caraway is an annual flowering plant indigenous to the Middle East and other regions of southwest Asia. Since antiquity, the seeds and other parts of the plant have been used as a remedy for many different ailments. More recently, there has been a revival of interest in the use of NS seeds and of various oils and other preparations derived therefrom, for the treatment of a large number of conditions and as a supplement for use in the maintenance of good health.

Among the therapeutic properties associated with, or attributed to, NS, the most widely known are its anti-inflammatory, anti-cancer, anti-bacterial, anti-fungal, blood pressure reducing and blood sugar lowering activities.

Many, but not all, of the pharmacologically active agents are present in the oil contained within the NS seed. In fact, the seeds of this plant contain two distinguishable oil fractions: fixed oil and essential oil, the latter containing a mixture of highly active volatile agents. Among these volatiles, one of the most highly active components is thymoquinone (TQ), and many of the pharmacological activities of NS oil-derived compositions are attributable to this agent.

The concentration of TQ within the NS seed is generally in the order of 0.3 to 1.0% (w/w), with differences seen between seeds obtained from different countries and regions. In some cases, however, the TQ content has been found to be as high as 2.5%. The cold-pressed oils obtained from these seeds predictably also contain only low levels of TQ, generally in the range of 0.5 to 1.5% (w/w).

Various different procedures have been developed for obtaining TQ-rich fractions from NS seeds. However, these procedures are often complex, lengthy and expensive. Also, in many cases, it is necessary to use solvent extraction or CO2 extraction steps, which may introduce selective extraction and complications related to the use of hazardous chemicals or expensive extraction processes.

A need thus exists for a simple method for preparing solvent-free compositions derived from NS seeds, wherein the concentration of TQ in said compositions is higher than previously obtainable in cold pressed NS oils. The present invention meets this need.

SUMMARY OF THE PRESENT INVENTION

The present invention is directed to a cold-pressed NS oil containing concentrations of TQ that are significantly higher than obtained in prior art NS oils of this type. Since many of the therapeutic and health-promoting activities of NS oils are related to their TQ content, the oil compositions of the present invention provide a significant technical advance, since, on the one hand, they possess high concentrations of the key active agent (TQ), while on the other hand, they are free from the safety, regulatory, cost-related and other disadvantages associated with prior art high-TQ NS extracts produced using solvent extraction techniques.

The present invention is thus primarily directed to a *Nigella sativa* (NS) cold press oil composition comprising thymoquinone (TQ) at a concentration of at least about 2% (w/w). In one preferred embodiment, said composition comprises TQ at a concentration of at least about 2.5% (w/w). In a further preferred embodiment, said composition comprises TQ at a concentration of at least about 3% (w/w).

One feature of the present invention is that the above-mentioned high concentrations of TQ (i.e. 2% or more) may be obtained even when the TQ concentration in the intact NS seeds is as low as 0.6% (w/w).

In another aspect, the composition of the present invention further comprises additional compounds present in the NS seed essential oil. Examples of such additional compounds include (but are not limited to) carvacrol, p-cymene and free fatty acids (FFAs). In many cases, the compositions of the present invention comprise both TQ and p-cymene, wherein the ratio of TQ to p-cymene is greater than 2.5:1. In some cases, this ratio is greater than 3:1. In one preferred embodiment, the TQ to p-cymene ratio is in the range of 2.5:1 to 7:1. In other preferred embodiments, the TQ to p-cymene ratio is in the range of 2.5:1 to 5:1. In still further preferred embodiments, this ratio is in the range of 2.67:1 to 4:1.

In many cases, the compositions of the present invention contain at least 0.75% p-cymene. In some embodiments, the p-cymene concentration is at least 0.8%, while in others, said concentration is at least 1%.

The concentration of carvacrol in the compositions of the present invention is generally less than 0.1% (w/w).

Many of the prior art cold pressed NS oil preparations contain free fatty acids (FFA) at relatively high concentrations (sometimes as high as 8% (w/w) or even higher). However, the present inventors have now found that optimal anti-inflammatory effects are achieved when the TQ concentration of the compositions is at least 2% (w/w) and when the FFA concentration is less than about 3% (w/w), and preferably less than about 2% (w/w).

In one preferred embodiment, the ratio of TQ to FFA in the composition is greater than 1.2:1.

Thus, in a preferred embodiment, the composition of the present invention comprises cold-pressed *Nigella sativa* (NS) oil, wherein said oil comprises thymoquinone (TQ) at a concentration of at least 2% (w/w), p-cymene at a concentration of at least 0.8% (w/w), carvacrol at a concentration of not more than 0.1% and FFA at a concentration of less than 3%.

The present invention is also directed to a process for preparing a NS seed oil containing TQ at a concentration of at least 2% (w/w), wherein said process comprises subjecting NS seeds to a cold press procedure using an oil press, wherein the pressure applied to said NS seeds during said cold press procedure is reduced to sub-optimum levels, thereby reducing the amount of oil produced from said seeds, while selectively increasing the concentration of TQ in said oil. Generally, the NS seed oil produced by this process will further comprise p-cymene. Preferably, the ratio between TQ and p-cymene in the seed oil is at least 2.5:1. Preferably, the FFA concentration of the oil produced by this process is less than 3% (w/w) and more preferably less than 2% (w/w).

The phrase "selectively increasing the concentration of TQ" is used herein to indicate that both the absolute concentration of TQ and the ratio of TQ to certain other volatile compounds in the cold-pressed oil (e.g. p-cymene) is increased. In other words, the increase in concentration of TQ is greater than the increase in these other compounds.

The term "sub-optimum" pressure levels, as used herein, refers to pressures exerted on the NS seeds by the cold press machine which are less than the pressure that is exerted when said machine is operated in accordance with the manufacturer's instructions, that is, when used in the normal manner in order to achieve maximum oil production.

Various means may be used to reduce the pressure applied to the NS seeds during the cold press procedure. In cases in which screw-driven oil press machines are used, the means may include (but are not limited to) increasing the exit nozzle aperture diameter and increasing the speed of rotation of the internal screw thread.

It is to be noted that the concentrations of TQ and p-cymene in the NS oil that are defined herein, refer to concentrations in the cold-pressed oil in the form in which it leaves the oil press. In other words, the concentrations recited herein refer to concentrations in cold-pressed oil that has not been further processed by means of being subjected to solvent extraction, supercritical carbon dioxide extraction or any other extraction or purification process.

In another aspect, the present invention is directed to a unit dosage form for oral administration comprising a composition as disclosed herein, wherein said unit dosage form is selected from the group consisting of a soft gel capsule, a hard-shell capsule, a bulk liquid, a tablet, a caplet, and other pharmaceutically acceptable oral dosage forms. In some cases, said composition is diluted with an oil diluent (e.g. a plant-based oil such as canola oil) prior to preparing the final dosage forms, thereby reducing the absolute concentration of the active ingredients present in the composition, but retaining the mutual weight ratios between these ingredients. Such diluted forms of the composition are also within the scope of the present invention.

The present invention also includes within its scope a composition comprising TQ, FFA, p-cymene and carvacrol, wherein the ratio of TQ to FFA is greater than 1.2:1 and the ratio of TQ to p-cymene is at least 2.5:1. This composition may be formulated as a unit dosage form for oral administration. Any suitable oral dosage form may be used for this purpose, including, but not limited to, a soft gel capsule, a hard-shell capsule, a bulk liquid, a tablet and a caplet.

DETAILED DESCRIPTION OF PREFERRED EMBODIMENTS

Figure 1:
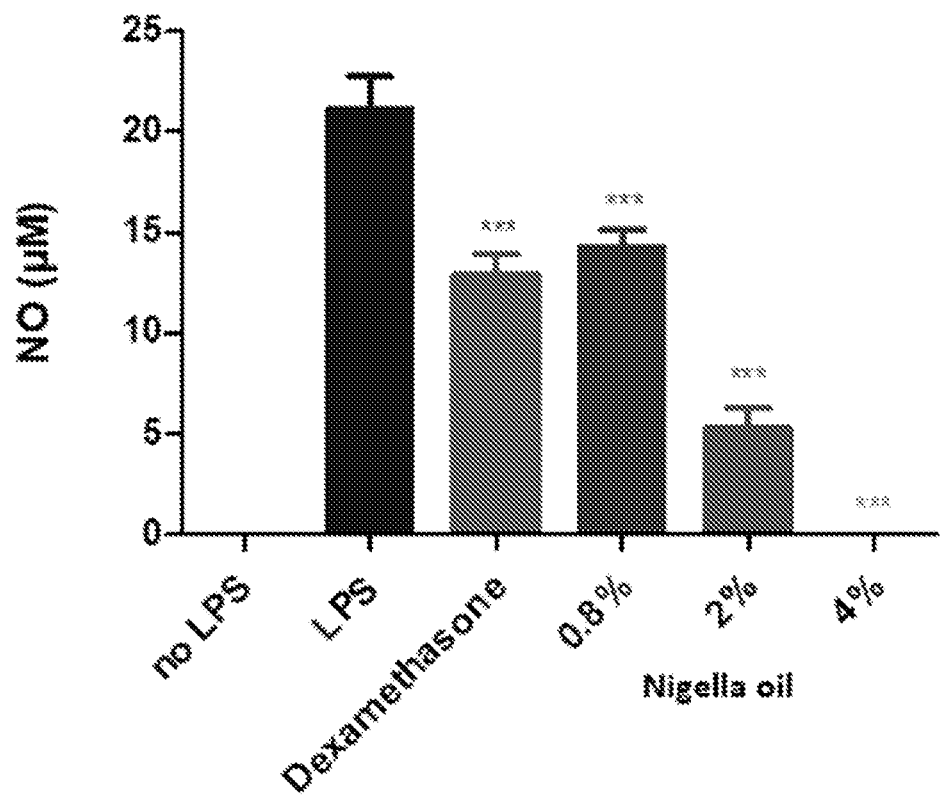
FIG. 1 is a bar graph showing the anti-inflammatory activity of NS oil containing three different concentrations of TQ as measured in a cell culture model of nitric oxide (NO) production.

Cold-pressed NS oils are commonly manufactured, on an industrial scale, using a screw-driven oil press. Generally, this type of press comprises a housing, in the central region of which is an elongate chamber. The seeds used for oil production are introduced into one end of the chamber and caused to move along the length of said chamber by means of a rotating screw shaft. In this way, the moving seeds are compressed between the screw shaft and the wall of the chamber. As a result of this compression, the oily components of the seeds are exuded therefrom, and the droplets of oil thus formed leave the chamber via an exit aperture, which may be fitted with a size-reducing nozzle in order to increase the outlet pressure.

Today, cold press oil is not standardized to TQ content at a level with a precision greater than ±0.3%, and as a result, the prior art preparations may have a TQ concentration within a very large range (0.3%-1.3%). This can be problematic, since the biological activity of cold-pressed NS oil in human and other species is dependent to a large degree on TQ concentration, and thus oils having a low TQ content may have a very low performance as an anti-inflammatory agent, In regular commercial use, it is important to extract the maximum possible amount of oil from the seeds, and thus the pressure conditions are optimized in order to achieve this aim. In general, it is possible to alter the pressure conditions experienced by the seeds within the press by means of altering one or both of the following operating parameters:

Speed of rotation of the screw shaft.
Diameter of the exit aperture nozzle.

Thus, it is possible to increase the percentage of the total oil that is extracted from the seeds by means of reducing the speed of screw shaft rotation—thereby increasing the time that the seeds spend in contact with the compressing surfaces in the chamber—and/or by means of reducing the exit aperture nozzle diameter.

The present inventors have now unexpectedly found that the concentration of TQ in cold-pressed oil obtained from NS seeds may be significantly elevated by means of one or both of the following changes in operating parameters:

Increasing the sped of screw shaft rotation.
Increasing the size of the exit aperture (by using either a larger diameter exit nozzle, or by entirely removing the nozzle).

Significantly, it was found by the present inventors that these changes in operating parameters result in a specific change (i.e. increase) in TQ concentration in cold-pressed NS oil. In other words, not all of the compounds present in the volatile oil fraction of the NS seed showed the same degree of increase in concentration. The observed change in TQ concentration is therefore a specific effect (rather than simply the result of reducing the total volume in which the oily components are exuded from the seeds).

Results demonstrating the increased TQ concentration obtained with various screw-thread oil press operating parameters are presented hereinbelow.

By using these altered operating parameters it is possible to prepare the compositions of the present invention as disclosed and claimed herein, wherein said compositions are primarily characterized by having a consistently high TQ concentration (at 2% (w/w)), p-cymene at a concentration of at least 0.8% (w/w), carvacrol at a maximum concentration of 0.1% (w/w) and FFA at a concentration of less than 3% (w/w).

The composition of the present invention possesses many biological activities, with a higher efficacy and/or potency than other cold-pressed NS oils of the prior art. In view of these activities, the composition of the present invention may be administered to (or taken by) both human and non-human mammalian subjects for the purpose of preventing or treating many different diseases and disorders. Thus, in a further aspect, the present invention is directed to a method for the treatment, prevention, attenuation or inhibition of the progression of an inflammatory disease or a disease having an inflammatory component in a mammalian subject, comprising the administration of a composition of the present invention, as disclosed hereinabove and described in more detail hereinbelow. In a preferred embodiment, the mammalian subject is a human subject.

The term 'a disease having an inflammatory component' should be understood as referring to any disease or health disorder, in which inflammatory processes may form part of the pathogenic process. These may include conditions which are not primarily considered to be inflammatory diseases, such as various types of neoplastic conditions and certain metabolic disorders (including type 2 diabetes), cardiac disease, and so on.

In some embodiments of the presently-disclosed method, the inflammatory disease may be selected from the group consisting of osteoarthritis, rheumatoid arthritis, pelvic inflammatory disease, atherosclerosis, periodontitis, ulcerative colitis, Crohn's disease, psoriasis, multiple sclerosis, AMD, other possible eye inflammatory related diseases, inflammatory bowel disease, rhinitis and other upper respiratory tract inflammatory conditions, adult respiratory distress syndrome (ARDS), asthma, cardiovascular inflammation, reperfusion injury, peritonitis, cirrhosis, inflammatory skin disorders including psoriasis, bullous diseases, eczema, allergic reactions in the skin, inflammatory conditions of the eyes, retinopathy, inflammatory conditions of infective origin, such as sepsis, trauma and other acute inflammatory conditions, chronic inflammatory conditions, allergies and hypersensitivity reactions of all of the various tissues, organs and organ systems.

In the method of treatment and/or prevention of the present invention, the daily dosage of TQ contained in the composition and administered to the subject may be in the range of 0.1-5,000 mg.

The present invention also encompasses a composition as defined herein for use as a medicament, nutraceutical, food supplement or in the preparation of a health food or beverage.

In another aspect, the present invention is directed to the use of a composition as described and defined herein in the preparation of a medicament for the treatment, prevention, attenuation or inhibition of the progression of an inflammatory disease or a disease having an inflammatory component, non-limiting examples of which are given hereinabove.

In one embodiment, the compositions may be orally administered in the form of soft gel capsules (SGC), hard shell capsule, tablets, caplets or in bulk oil form for oral administration on a spoon or other measuring utensil. Further details of the preparation of such formulations and dosage forms can be obtained from any standard reference on the subject, such as Remington's Pharmaceutical Sciences, Mack Publishing Co, Easton, Pa, USA, 21$^{st}$ edition (2006).

The compositions may also be formulated for oral administration in the form of drops for sublingual use. In addition, the compositions may be incorporated into sweets, candies, jellies, nutrition bars and other confectionaries and/or beverages.

It is to be noted that the aforementioned concentrations of TQ, p-cymene, carvacrol and FFA, and the weight or molar ratios therebetween are different from those that are found both in NS seeds and in cold-pressed NS oil prepared by the methods of the prior art. Said concentrations and ratios are a feature of the present invention. As will be shown in the Examples that follow, the modified concentrations and mutual weight ratios of these components result, in some cases, to a synergistic enhancement of the anti-inflammatory activity of the composition of the present invention. Thus, in some embodiments of the present invention, the composition disclosed and claimed herein is a synergistic anti-inflammatory composition.

Some of the key features and advantages of the present invention will now be exemplified in the following non-limiting Examples.

EXAMPLES

Example 1

Effect of Different Screw-Driven Oil Press Operating Conditions on the TQ and p-cymene Content of NS Cold Pressed Oil In this study, the effect of altering the pressure exerted on NS seeds by a screw-driven oil press on the TQ concentration of the NS oil product was investigated.

Methods:

The oil press used in this study was the Komet DD 85-G oil expeller (supplied by IBG Monforts Oekotec of Nordrhein-Westfalen, Germany).

NS seeds were obtained from two different locally-grown sources.

The effect of changing the oil press outlet pressure on the concentrations of TQ and another NS essential oil component, p-cymene, was investigated by means of either using different size exit nozzles (5, 8 or 12 mm), or by altogether removing the nozzle from the exit aperture. In addition, the effect of altering the screw shaft rotation speed was investigated by means of operating the oil press with different rotation speeds (22.2 rpm and 31.6 rpm)

The concentrations of TQ and p-cymene were measured in the NS oil produced by the screw-driven press, using a gas chromatography (GC-FID) method. Briefly, the analytical method was performed using a gas chromatograph system equipped with a flame ionization (FID) detector, autosampler and an integrating program. The GC column used was an RTx-5 ms 30 m*0.25 mm*0.25 µ, Cat no. 13423, Crossbond diphenyl dimethyl Polysiloxane (or equivalent) and the flame detection was performed at 280° C. The system was run using helium as the carrier gas at a flow rate of 2 ml/min. Typical retention times of the two NS oil components measured were as follows: p-Cymene 2.8 min; TQ 6.6 min. The oil samples were prepared for GC-FID as follows:

Weigh 0.5±0.05 g (accurate to 0.0001 g) oil sample into a 25 ml volumetric flask, add 10 ml acetone, mix well and fill to volume with acetone. Mix well again.

Filter the solution through a 0.45 µ filter into an autosampler vial

Inject into GC and report the peak area of every tested compound

In the case of the seed samples, the preparation was performed as follows:

Grind about 20 g of seeds using milling machine for 1 minute.

Weigh in duplicate 1.0±0.3 g (accurate to 0.0001 g) of ground seeds into a suitable glass bottle.

Add 50 ml of acetone and tightly close.

Put the sample bottle into the ultrasonic bath at room temperature for 30 min.

Filter the extract through a 0.45 µm filter into an autosampler vial

Inject into GC and report the peak area of every tested compound

The location of the peaks corresponding to p-cymene and TQ were identified using standard solutions of those two compounds (p-cymene: Acros, Code 111765500, Purity 99%; TQ: Aldrich. Cat. No. 274666, Purity 99%) prepared using acetone as the solvent. The integrating program was used to measure the concentrations of these compounds in the test (oil and seed0 samples by comparison with the areas of the standard solution peaks.

Results:

Table I, below, provides the TQ and p-cymene concentrations of different batches of cold-pressed NS oil, produced using the working conditions indicated:

TABLE I

| Cold press operating conditions: | p-Cymene % (w/w) | TQ % (w/w) | TQ %/ p-Cymene % | TQ % (w/w) in starting material (NS seeds) |
|---|---|---|---|---|
| No exit nozzle used: | | | | |
| 60% maximum speed | 0.99 | 3.09 | 3.12 | 0.5 |
| 80% maximum speed | 1.14 | 3.22 | 2.82 | 0.5 |
| Effect of different size exit nozzle: | | | | |
| 80% maximum speed No nozzle used | 1.33 | 3.68 | 2.76 | 0.84 |
| 80% maximum speed Size 12 nozzle | 1.07 | 3.06 | 2.86 | 0.84 |
| 80% maximum speed Size 7 nozzle | 1.07 | 2.94 | 2.75 | 0.84 |
| 40% maximum speed Size 8 nozzle | 0.92 | 2.57 | 2.79 | 0.84 |
| 40% maximum speed Size 5 nozzle | 0.89 | 2.39 | 2.69 | 0.84 |
| AVERAGE FOR ALL TEST CONDITIONS: | 1.06 (range = 0.89-1.33) | 2.99 (range = 2.39-3.68) | 2.83 (range = 2.69-3.12) | |

For the sake of comparison, Table II, below provides the TQ and p-cymene concentrations of eight different commercial NS cold-pressed oil compositions. This table also provides the free fatty acid (FFA) content of these compositions, as measured by a standard titration method (AOAC Official Method 940.28) published by AOAC International.

TABLE II

| Commercial formulation | Formulation type | p-Cymene avg % (w/w) | TQ avg % (w/w) | TQ %/ p-Cymene % | FFA by titration, % as oleic acid |
|---|---|---|---|---|---|
| Amazing Herbs | oil | 0.47 | 1.01 | 2.15 | 5.1% |
| GNC | oil | 0.39 | 0.54 | 1.38 | 4.7% |
| North American Spice Herbs | oil | 0.66 | 1.39 | 2.11 | 5.4% |
| Amazing Herbs | capsules | 0.36 | 0.82 | 2.28 | 6.4% |
| Amazing Herbs (1.32% TQ) | oil | 0.72 | 1.15 | 1.60 | 6.1% |
| Black seed oil Kolonje (BNB, India) | oil | 0.71 | 1.49 | 2.10 | 6.8% |
| Black seed oil, Pakistan | oil | 0.34 | 0.51 | 1.50 | 8.2% |
| Amazing Herbs (0.95% TQ) | oil | 0.68 | 1.57 | 2.31 | 5.9% |
| AVERAGE FOR ALL FORMULATIONS: | | 0.54 (range = 0.34-0.72) | 1.06 (range = 0.51-1.57) | 1.93 (range = 1.38-2.28) | 6.08 (range = 4.7-8.2) |

Comparison of the results obtained in the present study, using the modified oil press operating conditions (Table I), with the equivalent values obtained for prior art cold-press NS oil (Table II) indicates that these modified conditions lead to the production of NS oil characterized by having:

a) Higher levels of TQ (average of 2.99% (w/w), compared with 1.06% (w/w) for the prior art compositions tested).

b) Higher ratio of TQ/p-cymene (average of 2.83% (w/w), compared with 1.93% (w/w) for the prior art compositions tested.

A further characteristic of the cold-pressed oils of the present invention is the much lower concentration of FFAs than seen in commercial prior art preparations. Thus, as shown in Table II, above, the mean FFA concentration of the eight prior art preparations tested was 6.08. The comparable FFA concentrations of five separate batches of cold-pressed NS oil prepared according to the present invention are given below, in Table III:

TABLE III

| Batch no.: | FFA concentration (% w/w): |
|---|---|
| 1 | 0.9 |
| 2 | 1.5 |
| 3 | 1.4 |

TABLE III-continued

| Batch no.: | FFA concentration (% w/w): |
|---|---|
| 4 | 0.8 |
| 5 | 1.4 |
| Mean and range: | 1.2 (0.8-1.5) |

It may therefore be concluded that the modified oil press conditions (higher rotational speed of the screw shaft and/or larger oil exit aperture) enable the manufacture of NS cold press oil having a higher concentration of TQ. It is to be noted that these improved results were obtained using NS seeds having a TQ concentration of either 0.5 or 0.84% (w/w), i.e. TQ concentrations within the range normally found with most NS seed source material.

The fact that there is also an increased ratio between TQ and another NS volatile oil component (p-cymene) indicates that these operating conditions cause a specific increase in the TQ recovery that could not be accounted for simply in terms of the reduction in oil volume recovered from the seeds.

Example 2

Anti-Inflammatory Effect of a Composition of the Present Invention

The aim of this study was to evaluate the anti-inflammatory properties of cold-pressed NS oils containing different concentrations of TQ on the production of the inflammatory mediator, nitric oxide (NO), by murine macrophages (RAW 264.7 cell line) activated by lipopolysaccharide (LPS).

Methods:

$10^5$ RAW 264.7 cells were seeded in 96-well plates in (1% FBS, 1% Glutamine and 1% Pen/strep in DMEM).

Cells were treated with 4% NS oil (diluted 1:10,000), 2% NS oil ((diluted 1:10,000) or with 0.8% NS oil (diluted 1:10,000, Batch #21810328) for 22 hours together with LPS induction (5 ng/ml). In addition, positive control cells were treated with 20 μM dexamethasone. Nitric oxide (NO) release was tested after incubation at 37° C., 5% $CO_2$ using Griess Reagent System. The method is based on the chemical diazotization reaction that was originally described by Griess in 1879, which uses sulfanilamide and N-1-napthylethylenediamine dihydrochloride (NED) under acidic (phosphoric acid) conditions. This system detects $NO_2^-$ in a variety of biological and experimental liquid matrices such as tissue culture medium that was tested in this study.

The actual TQ percentage found in the 4% and 2% NS oils was 2.6% and 1.6% respectively. Therefore, cells were treated with equivalent dose levels of TQ found in the NS oils for 22 hours together with LPS induction (5 ng/ml). In addition, positive control cells were treated with 20 μM dexamethasone.

Results:

All NS oils demonstrated a reduction in NO release in a dose dependent manner. The chosen concentrations were found to be not cytotoxic. As shown in FIG. 1, each of the three different NS oils tested, as well as the dexamethasone positive control caused a significant reduction in NO release, as compared to the LPS-only treatment (***p<0.001, using one-way ANOVA). However, it is to be noted that these results indicate that while the 0.8% NS oil inhibited NO release to a similar degree to dexamethasone, the higher TQ concentrations oils (2% and 4%) caused far greater inhibition of this inflammatory mediator.

It may be concluded from these results that the degree of anti-inflammatory activity of NS oil is dependent on the TQ concentration, and that the NS oils having TQ concentrations of 2% or greater display far greater activity than seen with the commonly-used anti-inflammatory agent, dexamethasone.

Example 3

The Effect of Free Fatty Acid (FFA) Concentration on the Anti-Inflammatory Effect of a Composition comprising 2% TQ The aim of this study was to compare the anti-inflammatory effect of compositions of the present invention having different concentrations of FFA.

Methods:

Compositions comprising cold pressed NS oil containing a TQ concentration of 3% (w/w) were prepared according to the method described in Example 1, hereinabove. The FFA concentration of separate batches of this composition were adjusted by means of the addition of a commercial supercritical $CO_2$-extracted NS oil preparation (obtained from Ekologie Forte Pvt. Ltd.) containing 2.8% TQ and 50% FFA. The final FFA concentrations (% w/w) of the batches thus obtained were: 1.8%, 8%, 13%, 24%. The following dilutions of each of these different batches were then prepared by means of an initial 1:12 dilution in DMSO and then further dilution using RPMI 1640 culture medium containing 10% fetal calf serum, 2 mM L-glutamine and antibiotics:

1:500,000, 1:400,000, 1:300,000, 1:200,000, 1:100,000 and 1:50,000.

Each dilution was tested on the LPS-activated RAW 264.7 cell line model of NO production, as described in Example 2, hereinabove.

Figure 2:
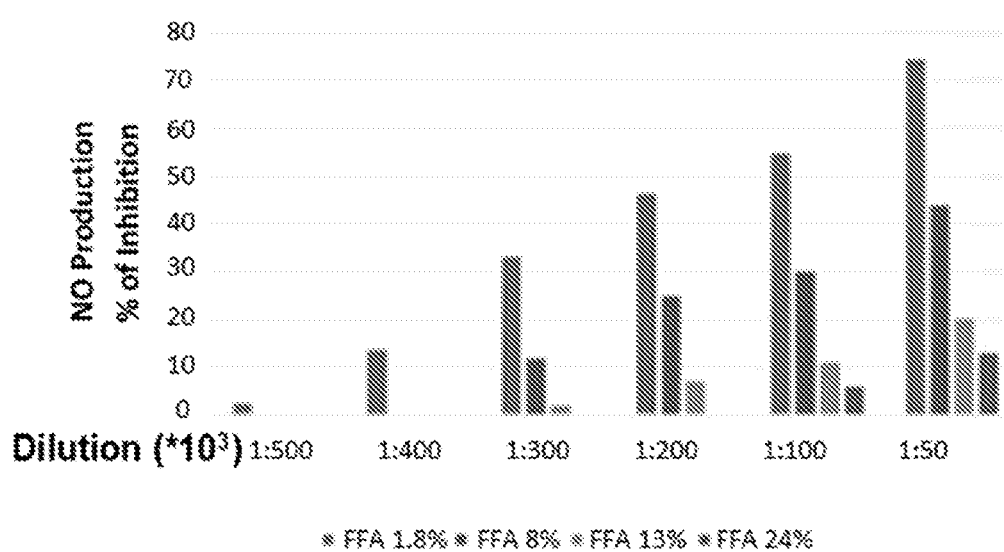
FIG. 2 is a bar graph showing the inverse relationship between the free fatty acid (FFA) content of NS oil compositions and the ability of said compositions to inhibit NO production.

Results:

FIG. 2 presents a series of bar graphs showing the NO-inhibitory activity of each of the dilutions, wherein this activity is presented as the percentage of inhibition (compared with the results obtained with a negative control composition containing no thymoquinone—results not shown).

It may be seen from this graph that at the lowest dilution (1:50,000), each of the four different compositions containing the different FFA concentrations produced a measurable inhibitor effect on NO production. Moving from left to right, the four bars shown at this dilution represent the results for the following FFA concentrations: 1.8%, 8%, 13% and 24%. It may clearly be seen at this dilution that there is an inverse relationship between the FFA concentration of the composition tested and its ability to inhibit NO. Thus, the greatest degree of inhibition (about 75% of maximum) is seen with the lowest FFA concentration (1.8%), with progressively lower levels of inhibition as the FFA concentration is increased to the maximum value (24%). A similar FFA dose-dependent relationship is seen at a dilution of 1:100,000. However, the absolute levels of NO inhibition for each dilution are lower than seen at the 1:50,000 dilution. This pattern is repeated at the higher dilutions; however, at dilution levels of 1:200,000 and 1:300,000, only the three lower concentrations of FFA produced any measurable inhibition of NO, while at dilutions of 1:400,000 and 1:500,000 only the lowest FFA concentration (1.8%) produced measurable inhibition.

These results clearly show that when combined with higher concentrations of FFA, compositions containing 3% TQ are unable to express their maximal anti-inflammatory effect. It is therefore important that compositions of the present invention, containing at least 2% TQ, have FFA concentrations as low as possible, preferably less than 8%, more preferably less than 3% and most preferably less than 2% (w/w).

Example 4

The Effect of the Concentration of Carvacrol on the Anti-Inflammatory Effect of a Composition comprising 2% TQ The aim of this study was to investigate the effect of the concentration of carvacrol on the anti-inflammatory activity of compositions comprising 2% TQ, using the same murine macrophage NO production model described in Examples 2-4, above.

Methods:

A solution of carvacrol was prepared and added to a stock solution of TQ in different amounts, in order to form three different test solutions, containing the following concentrations of the two agents:

2% TQ and 0.05% carvacrol
2% TQ and 0.1% carvacrol
2% TQ and 0.15% carvacrol
(All concentrations are given as w/w percent.)

In addition, a test solution containing only TQ (2%), and three test solutions containing carvacrol only (at the concentrations used in the above combinations) were also prepared.

Figure 3:
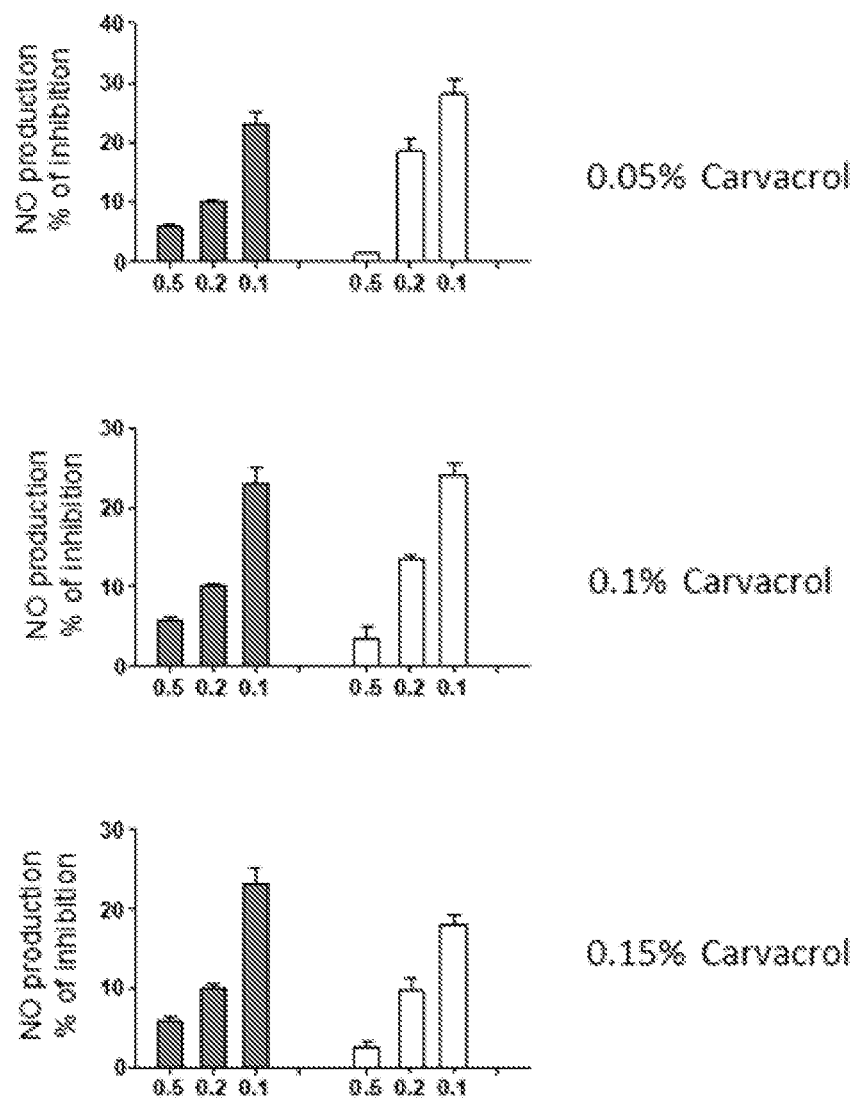
FIG. 3 is a bar graph showing the effect of different concentrations of carvacrol on the anti-inflammatory activity of a composition comprising 2% TQ.

Each of these solutions was then diluted to the following final dilutions in culture medium (after an initial 1:12 dilution in DMSO):

1:500,000, 1:200,000 and 1:100,000 (indicated as 0.5, 0.2 and 0.1, respectively, in FIG. 3).

Each of these dilutions was then tested for its ability to inhibit NO production in the murine macrophage cell line model described hereinabove in Example 2.

Results:

The results of this investigation are shown in FIG. 3.

None of the carvacrol-only dilutions caused any NO inhibition at the concentrations tested (data not shown).

The results for % maximum NO inhibition caused by 2% TQ alone (at each of the three dilutions tested) is represented by the sets of grey bars in the left region of each graph, while the white bars on the right side of each graph represent the results for the combinations of 2% TQ and carvacrol (at the concentrations and final dilutions indicated).

It may be seen from these results that at carvacrol concentrations of 0.1% and 0.05% the percentage maximum inhibition of NO is greater in the test combinations of TQ and carvacrol, for the 1:200,000 and 1:100,000 dilutions. Since carvacrol alone did not cause any NO inhibition, the increase in inhibitory activity seen in the combinations is indicative of a synergistic inhibition between carvacrol and TQ.

Conversely, it may be seen that when used at a higher concentration (0.15%) carvacrol appeared to cause a depression of the anti-inflammatory activity due to TQ when both agents were used in combination.

It may thus be concluded that in order to permit maximum expression of the anti-inflammatory activity of TQ when used at a concentration of 2%, it is important to restrict the concentration of carvacrol in the composition to 0.1% (w/w) or less.

Example 5

Synergistic Anti-Inflammatory Effect of Combinations of TQ and p-cymene

The aim of this study was to determine whether there is any synergistic interaction between TQ and p-cymene at the concentrations and mutual weight ratios in which these agents are present in the composition of the present invention.

Methods:

A solution of p-cymene were prepared and added to a stock solution of TQ in different amounts, in order to form four different test solutions, containing the following concentrations of the two agents:

2% TQ and 0.1% p-cymene
2% TQ and 0.25% p-cymene
2% TQ and 0.5% p-cymene
2% TQ and 0.75% p-cymene
(All concentrations are given as w/w percent.)

In addition, a test solution containing only TQ (2%), and four test solutions containing p-cymene only (at the concentrations used in the above combinations) were also prepared.

Each of these solutions was then diluted to a final dilution of 1:200,000 in culture medium (after an initial 1:12 dilution in DMSO).

Each of these solutions was then tested for its ability to inhibit NO production in the murine macrophage cell line model described hereinabove in Example 2.

Figure 4:
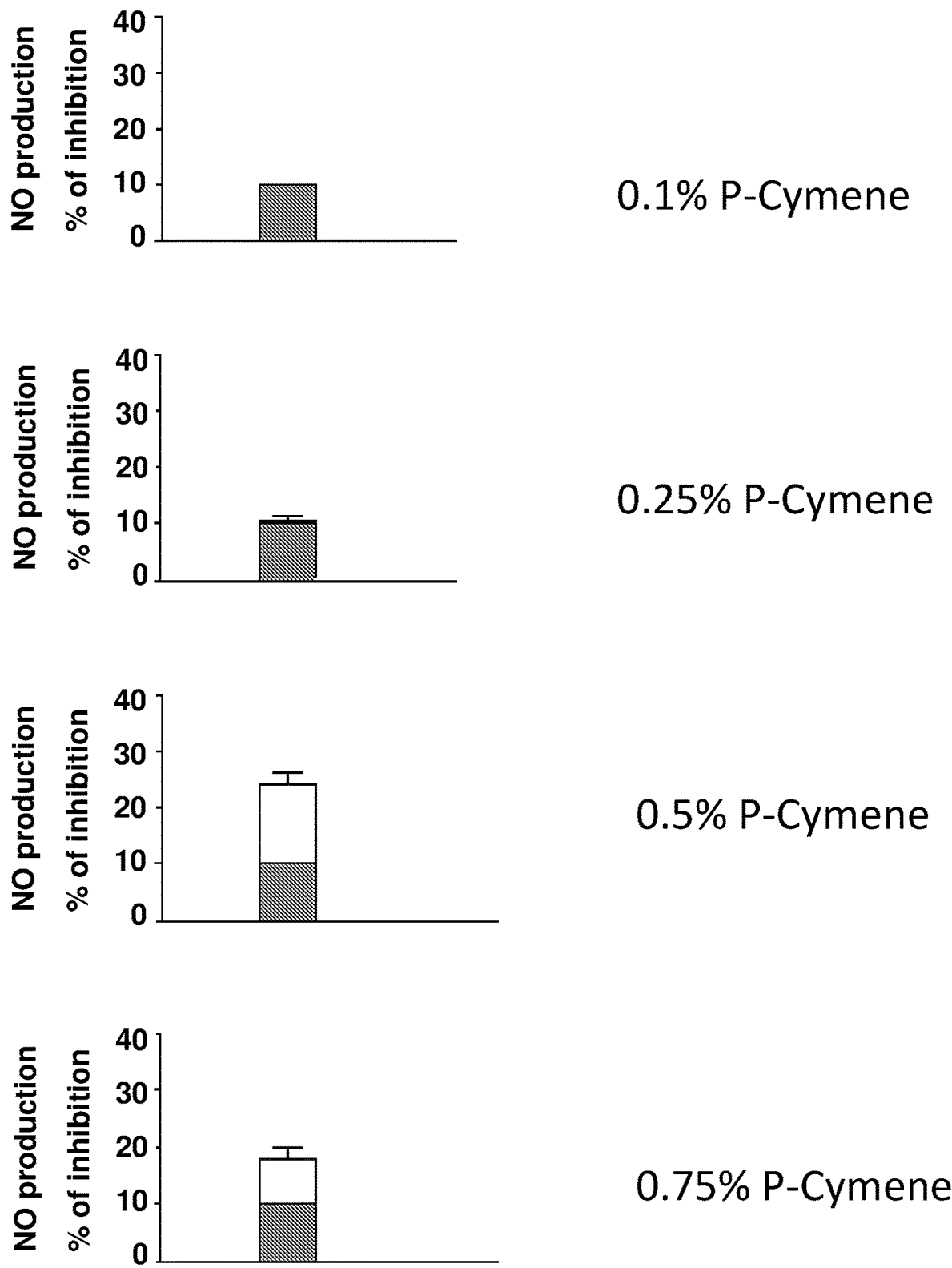
FIG. 4 is a bar graph demonstrating the synergistic interaction between TQ and p-cymene with respect to the inhibition of NO production.

Results:

The results of this investigation are shown in FIG. 4.

None of the p-cymene-only dilutions caused any NO inhibition at the concentrations tested (data not shown).

The results for % maximum NO inhibition caused by 2% TQ alone is represented by the upper border of the grey portion of each bar in the graphs shown in FIG. 4. In the combinations containing the two higher concentrations of p-cymene (0.5% and 0.75%), the presence of the latter agent caused an increase in NO inhibitory activity over and above that caused by 2% TQ alone (which, as mentioned, is shown by the height of the grey portions of the bars). Thus, in the lower two graphs, the NO production inhibitory activity has clearly increased considerably, in relation to the activity due to 2% TQ alone. This increase is represented by the height of the upper, unshaded regions of the two lower bars. Since, as mentioned above, p-cymene alone did not cause any inhibition of NO production, this increase is evidence of a synergistic interaction between TQ and p-cymene at the mutual weight ratios of these substances present in these two test solutions (i.e. 2% TQ/0.5% p-cymene and 2% TQ/0.75% p-cymene). The TQ: p-cymene weight ratios in these two synergistic combinations are 4:1 (for the 2% TQ/0.5% p-cymene combination) and 2.67:1 (for the 2% TQ/0.75% p-cymene).

No synergistic interaction between the two components was seen in the test combinations containing either 2% TQ/0.25% p-cymene (weight ratio 8:1) or 2% TQ/0.1% p-cymene (20:1).

Example 6

Comparative Example: Concentrations of Key Components in Extracted NS Oil Compositions Composition 1—Black Seed Oil CO2 Extract:
TQ 2.71%
FFA (as oleic acid) 16.5%
p-Cymene 1.25'%
Carvacrol 0.10%
Composition 2—BSOEA-380, 100 ml, Virgin Black Seed Oil. Natures Blends:
TQ 1.20%
FFA (as oleic acid) 6.4% p-Cymene 0.69%
Carvacrol 0.06%
Composition 3—Black Seed Oil CO2 Extract:
TQ 2.85%
FFA (as oleic acid) 46.5%
p-Cymene 1.22%
Carvacrol 0.12%

The ratios between TQ and FFA, and between TQ and p-cymene, as well as the carvacrol concentration of each of these prior art compositions and of a typical composition of the present invention are summarized in the following table:

TABLE IV

| Parameter: | PRESENT INVENTION | Comparative Composition 1 | Comparative Composition 2 | Comparative Composition 3 |
| --- | --- | --- | --- | --- |
| TQ: FFA | 2.1 | 0.17 | 0.19 | 0.06 |
| TQ: p-cymene | 2.75 | 2.17 | 1.74 | 2.34 |
| Carvacrol (% w/w) | 0.1 | 0.1 | 0.06 | 0.12 |

The invention claimed is:

1. A unit dosage form for oral administration, comprising a composition which comprises *Nigella sativa* (NS) oil, an oil diluent, p- cymene and carvacrol, wherein:
   said *Nigella sativa* oil comprises thymoquinone (TQ) at a concentration of at least 2% (w/w) and free fatty acids (FFA), and the ratio of TQ to FFA is greater than 1.2:1; the ratio of TQ to p-cymene is in a range of 2.5:1-4:1; and
   TQ and p-cymene of said composition synergistically inhibit NO production.

2. The unit dosage form according to claim 1, wherein the TQ concentration is at least 3% (w/w).

3. The unit dosage form according to claim 1, wherein the p-cymene concentration is at least 0.8% (w/w).

4. The unit dosage form according to claim 1, wherein the concentration of carvacrol is less than 0.1% (w/w).

5. The unit dosage form according to claim 1, wherein the concentration of FFA is less than 3% (w/w).

6. The unit dosage form according to claim 1, comprising *Nigella sativa* (NS) oil, wherein said oil comprises thymoquinone (TQ) at a concentration of at least 2% (w/w), p-cymene at a concentration of at least 0.8% (w/w), carvacrol at a concentration of not more than 0.1% and FFA at a concentration of less than 3% (w/w).

7. The unit dosage form according to claim 1, wherein said unit dosage form is selected from the group consisting of a soft gel capsule, a hard-shell capsule, a bulk liquid, a tablet, a caplet, and other pharmaceutically acceptable oral dosage forms.

* * * * *